(12) United States Patent
Mande et al.

(10) Patent No.: US 11,688,519 B2
(45) Date of Patent: Jun. 27, 2023

(54) METHOD AND SYSTEM FOR MONITORING THE GUT HEALTH OF AN INDIVIDUAL

(71) Applicant: Tata Consultancy Services Limited, Mumbai (IN)

(72) Inventors: Sharmila Shekhar Mande, Pune (IN); Swadha Anand, Pune (IN); Chandrani Das, Pune (IN); Kuntal Kumar Bhusan, Pune (IN); Harrisham Kaur, Pune (IN)

(73) Assignee: TATA CONSULTANCY SERVICES LIMITED, Mumbai (IN)

(*) Notice: Subject to any disclaimer, the term of this patent is extended or adjusted under 35 U.S.C. 154(b) by 797 days.

(21) Appl. No.: 16/032,857

(22) Filed: Jul. 11, 2018

(65) Prior Publication Data
US 2019/0139645 A1    May 9, 2019

(30) Foreign Application Priority Data
Jun. 29, 2017  (IN) .............................. 201721022811

(51) Int. Cl.
| | |
|---|---|
| *G16H 50/30* | (2018.01) |
| *C12Q 1/689* | (2018.01) |
| *C12Q 1/6886* | (2018.01) |
| *C12Q 1/6883* | (2018.01) |
| *G16H 50/20* | (2018.01) |
| *G16B 10/00* | (2019.01) |
| *G16B 45/00* | (2019.01) |
| *G16B 5/20* | (2019.01) |
| *G16B 40/10* | (2019.01) |
| *C12Q 1/6809* | (2018.01) |
| *C12Q 1/6825* | (2018.01) |

(52) U.S. Cl.
CPC ............. *G16H 50/30* (2018.01); *C12Q 1/689* (2013.01); *C12Q 1/6809* (2013.01); *C12Q 1/6825* (2013.01); *C12Q 1/6883* (2013.01); *C12Q 1/6886* (2013.01); *G16B 5/20* (2019.02); *G16B 10/00* (2019.02); *G16B 40/10* (2019.02); *G16B 45/00* (2019.02); *G16H 50/20* (2018.01)

(58) Field of Classification Search
None
See application file for complete search history.

(56) References Cited

U.S. PATENT DOCUMENTS

2014/0093478 A1    4/2014  Tumbaugh et al.

OTHER PUBLICATIONS

Anand, S.; Kaur, H.; Mande, S. S. Comparative In Silico Analysis of Butyrate Production Pathways in Gut Commensals and Pathogens. Front. Microbiol. 2016, 7.*

(Continued)

*Primary Examiner* — Soren Harward
(74) *Attorney, Agent, or Firm* — Finnegan, Henderson, Farabow, Garrett & Dunner LLP

(57) ABSTRACT

A system and method for predicting gut health of an individual using non-invasive technique has been provided. The system is making use of two types of pathways i.e. one which are beneficial to gut health and the second which are harmful to gut health. These two types of pathways are annotated in the genomes of gut bacteria. Best combinations of subsets of these pathways capable of distinguishing between gut commensals and pathogens are assigned as pathway biomarkers. The identified pathway biomarkers are then used to develop scheme for prediction of gut health status.

8 Claims, 10 Drawing Sheets

(56) References Cited

OTHER PUBLICATIONS

Fortune, K. J.; Beaumont, M.; Davila, A.-M.; Tomé, D.; Blachier, F.; Sanz, Y. Gut Microbiota Role in Dietary Protein Metabolism and Health-Related Outcomes: The Two Sides of the Coin. Trends in Food Science & Technology 2016, 57, 213-232.*

Winter, S. E. Mechanisms of Dysbiosis in the Inflamed Gut. In Host—Pathogen Interaction; Unden, G., Thines, E., Schüffler, A., Eds.; Wiley-VCH Verlag GmbH & Co. KGaA: Weinheim, Germany, 2016; pp. 77-92.*

Finn, R. D.; Bateman, A.; Clements, J.; Coggill, P.; Eberhardt, R. Y.; Eddy, S. R.; Heger, A.; Hetherington, K.; Holm, L.; Mistry, J.; Sonnhammer, E. L. L.; Tate, J.; Punta, M. Pfam: The Protein Families Database. Nucleic Acids Research 2014, 42 (D1), D222-D230.*

KEGG. Alanine, Aspartate and Glutamate Metabolism Diagram. Mar. 8, 2018.*

KEGG. Histidine Metabolism Diagram. May 10, 2018.*

Costello, E. K.; Lauber, C. L.; Hamady, M.; Fierer, N.; Gordon, J. I.; Knight, R. Bacterial Community Variation in Human Body Habitats Across Space and Time. Science 2009, 326 (5960), 1694-1697.*

Nieuwdorp, "Gut microbiota composition: A new kind of biomarker?," *Gut Microbiota for Health*, World Summit 2016, 6 pages, http://www.gutmicrobiotaforhealth.com/wp-content/uploads/2016/02/20160218_Fact-sheet-biomarker_en.pdf.

Xiao, et al. "Gut microbiota-based translational biomarkers to prevent metabolic syndrome via nutritional modulation," *FEMS Microbiology Ecology Federation of European Microbiological Societies*, vol. 87, issue (2), pp. 303-314, https://www.ncbi.nlm.nih.gov/pmc/articles/PMC4262049/pdf/tem0087-0303.pdf.

\* cited by examiner

METHOD AND SYSTEM FOR MONITORING THE GUT HEALTH OF AN INDIVIDUAL

PRIORITY CLAIM

This U.S. patent application claims priority under 35 U.S.C. § 119 to: India Application No. 201721022811 filed on 29 Jun. 2017. The entire contents of the aforementioned application are incorporated herein by reference.

TECHNICAL FIELD

This disclosure relates generally to the field of monitoring health of an individual, and more particularly method and system for monitoring and predicting gut health of the individual using pathway biomarkers.

BACKGROUND

The advent of metagenomics has led to significant advances in understanding the bacterial microbiome in symbiotic association with different body sites in humans. Gastro-intestinal (GI) tract is the major site of bacterial colonization and it is well established that taxonomic constitution of gut microbiome influences gut health of the host. The microbiota residing within/on the human body is repeatedly being proven to be a significant modulator of health. The pathogens represent bacteria harmful to gut while commensals represent beneficial or symbiotic gut bacteria.

The beneficial effect of the resident microbiome of gastrointestinal tract (gut), in terms of nutrient assimilation, immuno-modulation etc., is well established in the art. Metabolites biosynthesized by gut bacteria, like short chain fatty acids (SCFAs) (such as Butyrate and Propionate) have been shown to exert anti-inflammatory effects on the host. On the other hand, dysbiosis in the gut microbiome has been associated with several diseases like obesity, diabetes, inflammatory bowel disease, colorectal cancer, malnourishment etc. Thus, it becomes important to understand functional role of gut microbiome in healthy and dysbiotic diseased state.

One of the detrimental effects of pathogenic bacteria in gut microbiome has been attributed to their ability to ferment undigested proteins. Several products/by-products of this fermentation process, such as Ammonia, p-Cresol, Putrescine, Indole, Phenol etc. have been suggested to have deleterious consequences for the enteric health. In addition, few pathways producing beneficial metabolites like SCFA also involve amino acid fermentation that lead to Ammonia release which has been shown to elevate the inflammatory response in the gut.

Thus, not only the beneficial/harmful products, but also the pathways that bacteria utilize for their production forms a crucial basis to assess the metabolic capabilities of gut microbiome. Given the importance of gut microbiome in preserving physiological and metabolic homeostasis, their functional potential can be harnessed to evaluate gut health status. The prediction of functional potential requires accurate annotation of pathways within the microbiota of an individual.

The prior methods for assessing gut health based on microbiome include taxonomic biomarkers. Metagenomic sequencing has been extensively used for assignment of taxonomic composition in a sample and differentially abundant taxa (healthy vs. diseased) have been associated to different diseases. These taxonomy based biomarkers might differ with the demographic location and the dietary pattern of the population. Thus, a taxonomic biomarker identified for a particular geography might not prove efficient for a different region/geography.

Another method involves metabolite detection in the fecal samples. The presence of certain metabolites (like SCFAs, Ammonia, etc.) in fecal matter is used to profile metabolic repertoire of the gut microbiota. These methods do not account for the metabolic pathways involved in their production as well as members of gut microbiome contributing towards the biosynthesis of these metabolites. Further, these methods fail to identify by-products of these pathways which might be deleterious to gut health.

SUMMARY

Embodiments of the present disclosure present technological improvements as solutions to one or more of the above-mentioned technical problems recognized by the inventors in conventional systems. In view of the foregoing, an embodiment herein provides a system for predicting gut health of an individual. The system comprises an input module, an extractor, a sequencer, an organism pathway matrix, a memory and a processor. The input module obtains gut sample of the individual at two time stamps, a time stamp 1 and a time stamp 2. The extractor extracts nucleic acid from the obtained sample. The sequencer sequences the sample to generate a plurality of nucleotide sequences. The organism pathway matrix organisms comprises a set of Ammonia releasing pathways as biomarker for pathogens and a Pyruvate pathway as biomarker for commensals. The processor further comprises an Ammonia releasing pathway abundance calculation module, a Pyruvate pathway abundance calculation module, a first ratio calculation module, a second ratio calculation module, an Ammonia median evaluation module, a Pyruvate median evaluation module and a health status prediction module. The Ammonia releasing pathway abundance calculation module obtains cumulative abundance of the set of Ammonia releasing pathways from the plurality of nucleotide sequences using the 'organism-pathway matrix'. The Pyruvate pathway abundance calculation module obtains cumulative abundance of the Pyruvate pathway from the plurality of nucleotide sequences using the 'organism-pathway matrix'. The first ratio calculation module calculates a first ratio of the cumulative abundance of the set of Ammonia releasing pathways based on the values in the two time stamps. The second ratio calculation module calculates a second ratio of the cumulative abundance of the Pyruvate pathway based on the values in two time stamps. The Ammonia median evaluation module evaluates an Ammonia median of the cumulative abundance of the set of Ammonia releasing pathways. The Pyruvate median evaluation module evaluates a Pyruvate median of the cumulative abundance of the Pyruvate pathway. The health status prediction module predicts the gut health status of the individual based on a predefined criteria using the first and the second ratios, the Ammonia median and the Pyruvate median.

Another embodiment provides a processor implemented method for predicting gut health of an individual. Initially, the gut sample of the individual is obtained at two time stamps, a time stamp 1 and a time stamp 2. In the next step, nucleic acid is extracted from the obtained samples. In the next step, the obtained samples are sequenced using a sequencer to generate a plurality of nucleotide sequences. In the next step, an 'organism-pathway matrix' is obtained, wherein the matrix comprising a set of Ammonia releasing pathways as biomarker for pathogens and Pyruvate pathway as biomarker for commensals. In the next step, a cumulative abundance of the set of Ammonia releasing pathways is obtained from the plurality of nucleotide sequences using the 'organism-pathway matrix'. Similarly, a cumulative abundance of the Pyruvate pathway is also obtained from the plurality of nucleotide sequences using the 'organism-pathway matrix'. In the next step, a first ratio of the cumulative abundance of the set of Ammonia releasing pathways is calculated based on the values in the two time stamps. Similarly, a second ratio of the cumulative abundance of the Pyruvate pathway is also calculated based on the values in two time stamps. In the next step, an Ammonia median of the cumulative abundance of the set of Ammonia releasing pathways is evaluated. Similarly, a Pyruvate median of the cumulative abundance of the Pyruvate pathway is also evaluated. And finally the gut health status of the individual is predicted based on a predefined criteria using the first and the second ratios, the Ammonia median and the Pyruvate median.

In another embodiment, a non-transitory computer-readable medium having embodied thereon a computer program for predicting gut health of an individual. Initially, the gut sample of the individual is obtained at two time stamps, a time stamp 1 and a time stamp 2. In the next step, nucleic acid is extracted from the obtained samples. In the next step, the obtained samples are sequenced using a sequencer to generate a plurality of nucleotide sequences. In the next step, an 'organism-pathway matrix' is obtained, wherein the matrix comprising a set of Ammonia releasing pathways as biomarker for pathogens and Pyruvate pathway as biomarker for commensals. In the next step, a cumulative abundance of the set of Ammonia releasing pathways is obtained from the plurality of nucleotide sequences using the 'organism-pathway matrix'. Similarly, a cumulative abundance of the Pyruvate pathway is also obtained from the plurality of nucleotide sequences using the 'organism-pathway matrix'. In the next step, a first ratio of the cumulative abundance of the set of Ammonia releasing pathways is calculated based on the values in the two time stamps. Similarly, a second ratio of the cumulative abundance of the Pyruvate pathway is also calculated based on the values in two time stamps. In the next step, an Ammonia median of the cumulative abundance of the set of Ammonia releasing pathways is evaluated. Similarly, a Pyruvate median of the cumulative abundance of the Pyruvate pathway is also evaluated. And finally the gut health status of the individual is predicted based on a predefined criteria using the first and the second ratios, the Ammonia median and the Pyruvate median.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Figure 1:
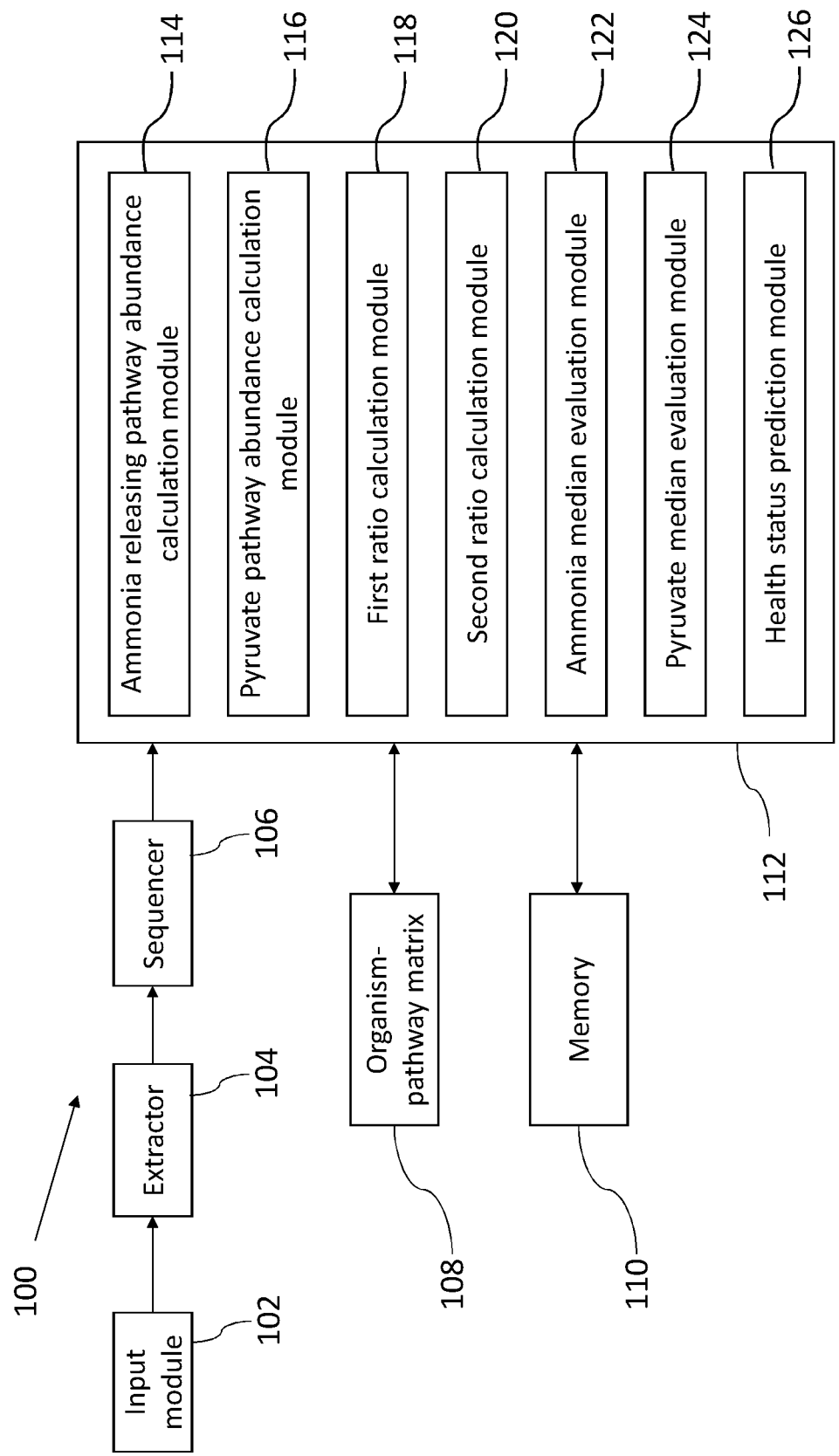
FIG. 1 shows a block diagram of a system for predicting gut health of an individual in accordance with an embodiment of the disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

Referring now to the drawings, and more particularly to FIG. 1 to FIG. 8, where similar reference characters denote corresponding features consistently throughout the figures, there are shown preferred embodiments and these embodiments are described in the context of the following exemplary system and/or method.

FIG. 1 illustrates a schematic block diagram of a system 100 for predicting gut health of an individual using non-invasive techniques. The system 100 is making use of two types of pathways i.e. one which are beneficial to gut health and the second which are harmful to gut health. These two types of pathways are annotated in the genomes of gut bacteria using Hidden Markov Model (HMM) based analysis. It should be appreciated that analysis using any other model is well within the scope of this disclosure. Best combinations of subsets of these pathways capable of distinguishing between gut commensals and pathogens are assigned as pathway markers which are further used to develop a scheme for prediction of gut health status.

The system 100 comprises an input module 102, an extractor 104, a sequencer 106, an organism-pathway matrix 108, a memory 110 and a processor 112 in communication with the memory 110. The processor 112 is configured to read algorithms stored in the memory to perform various functions. The processor 112 further includes a plurality of modules for performing various functions. The plurality of modules comprises an Ammonia releasing pathway abundance calculation module 114, a Pyruvate pathway abundance calculation module 116, a first ratio calculation module 118, a second ratio calculation module 120, an Ammonia median evaluation module 122, a Pyruvate median evaluation module 124 and a health status prediction module 126.

The input module 102 is configured to act as input user interface for the system 100. The input module 102 is configured to obtain the samples from the gut of the individual at two time stamps, i.e., a time stamp 1 and a time stamp 2. It should be appreciated that the time stamp1 and the time stamp 2 are corresponding to any two different time points. For example, samples can be obtained at two different time points during routine health screening of the said individual, during health screening of the said individual as prescribed by a health consultant/medical practitioner, during the course of any treatment regime of the said individual, etc. In another embodiment, the gut samples corresponding to time stamp 1 and the time stamp 2 refer to the gut samples of two different individuals. In another embodiment, the time stamp1 and the time stamp 2 are corresponding to two different population data where the gut health of two population are being compared.

In an embodiment of the disclosure, the gut samples are obtained from at least one of stool, swab, tissue, fluid of the individual. It should be appreciated that the samples can be obtained from amplicon sequencing or metagenomic sequencing. In another embodiment, the sample can also be obtained using techniques like Polymerase Chain Reaction (PCR), wherein each gene of the mentioned pathways is amplified using primers. Further, the sample can also be obtained from expression data of the constituent genes of the mentioned pathways. In an example, the input module 102 can be referred as the user interface or input/output interface 102. The I/O interface user may allow the system 100 to interact with the user directly or through the client devices. The input module 102 can facilitate multiple communications within a wide variety of networks and protocol types, including wired networks, for example, LAN, cable, etc., and wireless networks, such as WLAN, cellular, or satellite. The input module 102 may include one or more ports for connecting a number of devices including assistive technology devices or adaptive products used by people with disability to one another or to another server.

The samples received from the input module 102 is utilized to extract nucleic acid using the extractor 104. Further, the DNA samples are then sequenced using the sequencer 106. The sequencing is performed using high-throughput sequencing techniques. The sequencing results in the generation of a plurality of nucleotide sequences.

Figure 2:
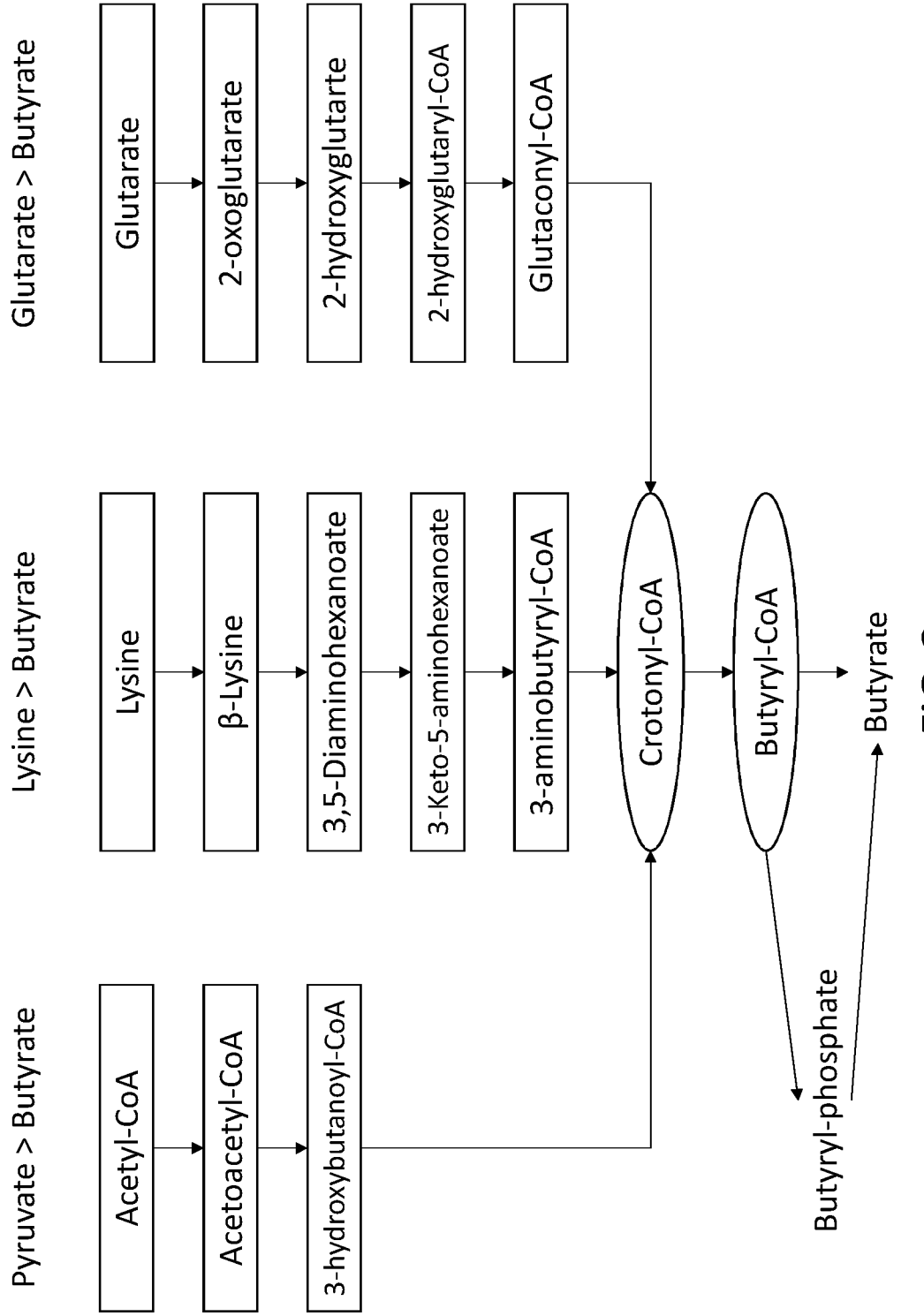
FIG. 2 shows the Pyruvate to Butyrate, Lysine to Butyrate and Glutarate to Butyrate pathways in accordance with an embodiment of the disclosure.
Figure 3:
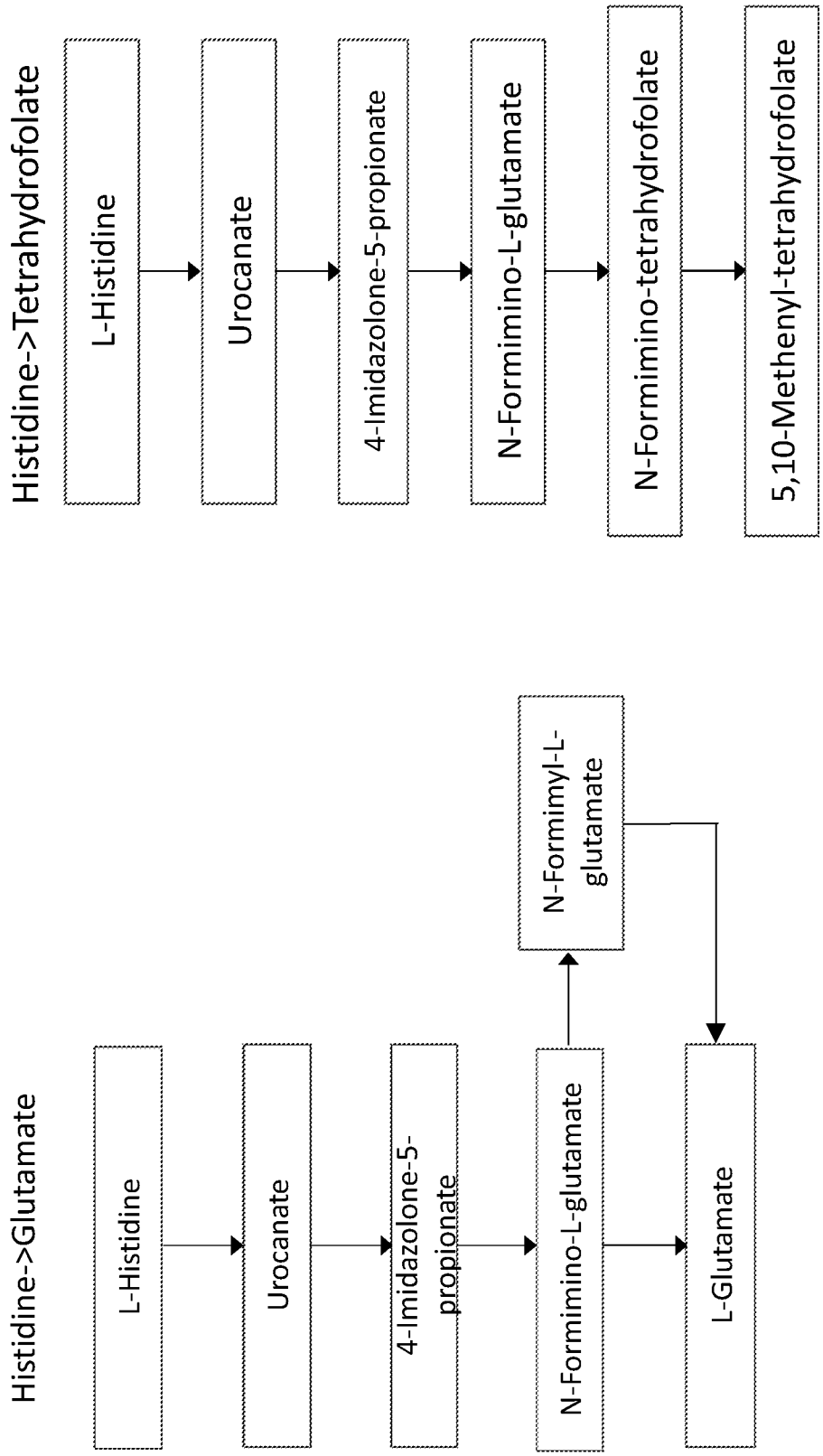
FIG. 3 shows Histidine to Glutamate and Histidine to Tetra-hydro folate pathways in accordance with an embodiment of the disclosure.

According to an embodiment of the disclosure, the system 100 is utilizing a set of Ammonia releasing pathways as biomarker for pathogens and Pyruvate pathway as biomarker for commensals. It should be appreciated that the set of Ammonia releasing pathways correspond to one or more of Histidine→Glutamate, Histidine→Tetrahydro folate (THF), Lysine→Butyrate and Glutarate→Butyrate as shown in FIG. 2 and FIG. 3. The Pyruvate pathway (Pyruvate→Butyrate) is shown in FIG. 2. It should be appreciated the system 100 is not limited to utilizing only the above mentioned pathways. For instance, any other amino acid oxidation pathway can be utilized as the biomarker for pathogens.

Though it should be appreciated that for the sake of clarity and better understanding, the present disclosure will be using the set of Ammonia releasing pathways and Pyruvate pathway to predict the gut health of the individual.

Figure 4:
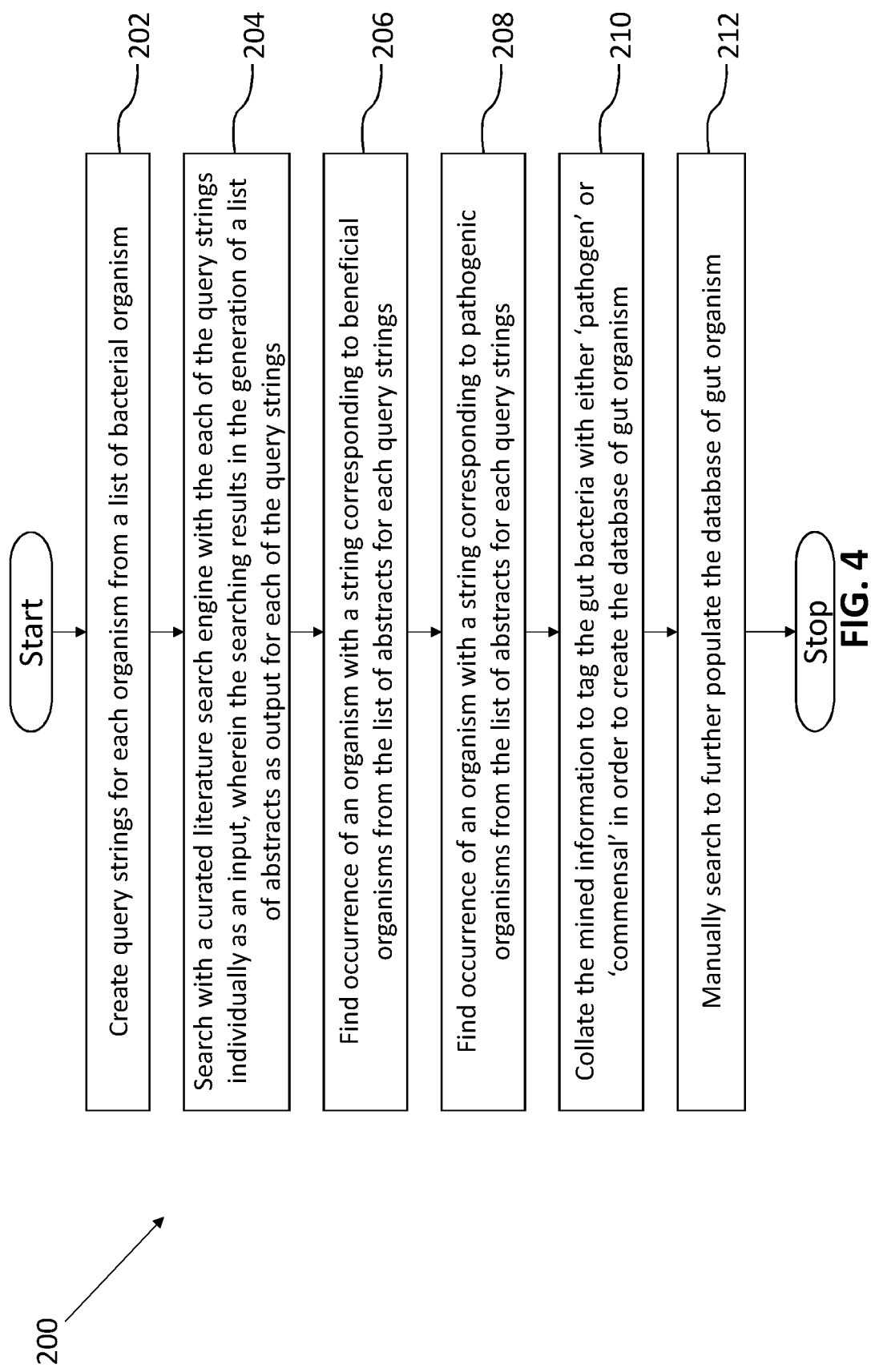
FIG. 4 shows a flowchart for creating a database of gut organisms according to an embodiment of the disclosure.

According to an embodiment of the disclosure, a database of gut organism DGO is created using a literature mining strategy as shown in the flowchart 200 of FIG. 4. Initially at step 202, a search query string $Q_n$ is created for each organism n from a list of genomes. In the present example, complete bacterial genomes in the NCBI database are used. Thus the query will look like as follows:

['NameString']+[(Gut) OR (Enteric) OR (Gastrointestinal)]

The use of any other synonym or any other variations of this search string are well within the scope of this disclosure.

In the next step 204, a curated literature search engine like Pubmed is used with Query string $Q_n$ as input and obtain list of abstracts $A_n$ as output for each Query string Qn. Then at step 206, each of the list $A_n$ is used to find occurrence of organism n with string 'commensal' or 'beneficial'. In the next step 208, each of the list $A_n$ is used to find occurrence of organism n with string 'pathogen' or 'harmful' or 'disease'. At step 210, the findings of the occurrence of organism corresponding to pathogenic and commensal organisms are collated to create the database of gut organism. And finally at step 212, a manual search may also be used to further populate the Database of Gut Organisms DGO. A hash DGO was also created corresponding to this database where the keys are organism names and the values are either 'P' (pathogen) or 'C' (commensal).

According to an embodiment of the disclosure, the system 100 is further configured to create a genome pathway matrix. Initially at step 302 a database 'DS' of sequences is created from representative genomes where Pyruvate (Pyruvate→Butyrate) and putrefaction pathways (Glutarate→Butyrate, Lysine→Butyrate, 4-amino-butyrate→Butyrate, Histidine→Glutamate, Histidine→Tetra-hydro folate, Tryptophan→Indole, Tyrosine→Phenol, Arginine→Putrescine, Tyrosine→Cresol) addressed in the disclosure have been experimentally characterized. The sequences in 'DS' correspond to the proteins involved in the above mentioned pathways. In the next step 304, a HMM based search is performed on DS to identify the corresponding Pfam domains and store these domains in a database DPF. Any other homology search/annotation method as well as domain/protein database are well within the scope of the invention. The Pfam domains thus identified are stored in a database 'DPF'. At step 306, a hash PD is created with key as pathway (P) and corresponding list of PFAMs as values.

In the next step 308, a HMM based protein search is performed on DGO using DPF as domain database. Any other homology search/annotation method as well as domain/protein database are well within the scope of the invention. At step 310, for each genome G in DGO a location array LAG is created using a location map of genome as reference (obtained from 'ptt file' provided in NCB' database in this case). Similarly, for each key P in hash PD, all the values (which are Pfams in this implementation) which lie within a window of 10 genes of each other using LAG for a genome G as reference are considered. At step 312, a matrix M is created with genome names and pathways, with value as 0 if pathway Pfams are absent within a window of 10 genes of LAG and value as 1 if pathway Pfams are present within 10 genes of LAG. Further at step 314, a commensal sub-matrix MC from the matrix M is extracted with genomes having Pyruvate pathway value as one. Similarly at step 316, a pathogen sub-matrix MP from the matrix M is extracted with genomes having Ammonia releasing pathway value as one.

According to an embodiment of the disclosure, the system 100 is further configured to find the best combination of the set of pathways capable of differentiating commensals and pathogens. Initially, a sub-matrix MC from M is extracted with genomes having Pyruvate pathway value as 1. Each genome in sub-matrix MC was mapped against the keys of the hash DGO and the corresponding values were noted. The Pyruvate pathway (as depicted in FIG. 2) is observed to have absolute correlation with the commensal gut bacteria.

Further all possible unique combinations were built with two to eight of the putrefaction pathways. For each combination, a sub-matrix MP from M is extracted with genomes having value for at least one of the pathway as 1. Each genome in sub-matrix MP was then mapped against the keys of the hash DGO and the corresponding values were noted. The set of four pathways (Lysine→Butyrate, Glutarate→Butyrate, Histidine→Glutamate and Histidine→Tetra-hydro folate) were obtained as an optimal set which could represent pathogenic gut bacteria (as listed in DGO). These four pathways have been depicted in FIG. 2 and FIG. 3.

According to an embodiment of the disclosures, the system 100 is also configured to calculate the cumulative abundance of the set of Ammonia releasing pathways and the Pyruvate pathway using the Ammonia releasing pathway abundance calculation module 114 and the Pyruvate pathway abundance calculation module 116 respectively. If the sample has been sequenced from marker gene, the step of calculating the cumulative pathway abundance further comprising: Initially, the input matrices M1 and M2 of genus abundances are provided for the individual at two time stamps or a population with one matrix representing healthy sub-population and other representing a dysbiotic sub-population (or two stages of a disease during treatment). The pathway abundance matrix for commensal can be calculated as follows:
Commensal pathway abundance matrix AM1C corresponding to genus abundance matrix M1=MC*M1
Commensal pathway abundance matrix AM2C corresponding to genus abundance matrix M2=MC*M2.

Similarly, the pathway abundance matrix for pathogen can be calculated as follows:
Pathogenic pathway abundance matrix AM1P corresponding to genus abundance matrix M1=MP*M1
Pathogenic pathway abundance matrix AM2P corresponding to genus abundance matrix M2=MP*M2.

According to an embodiment of the disclosure, if the sample has been sequenced from at least one of metagenome, gene expression data or obtained from primer amplification (PCR), the step of calculating the cumulative pathway abundance further comprising. Firstly, cumulative gene abundance is calculated for pathogen pathways. Followed by calculation of cumulative gene abundance for commensal pathways.

Figure 6:
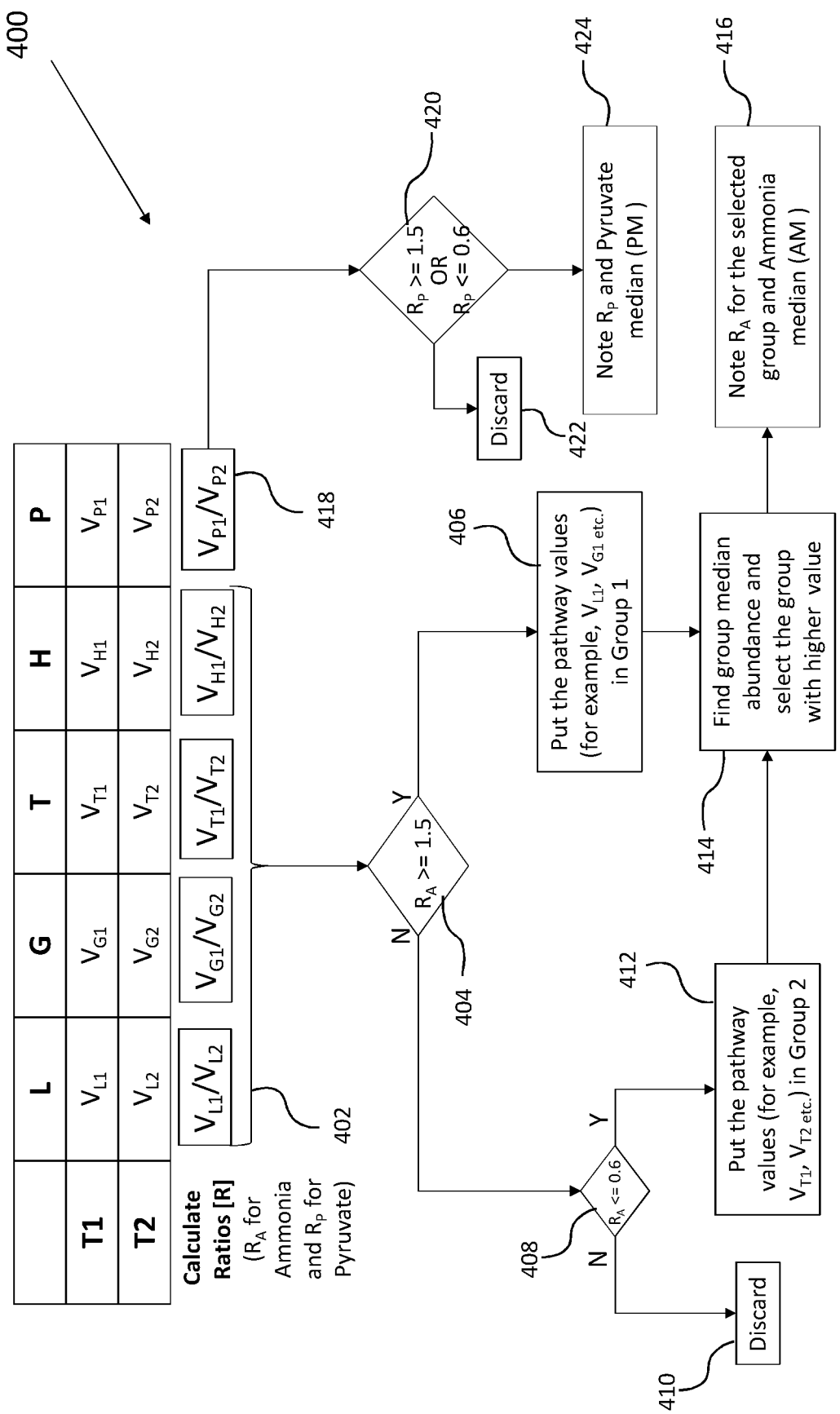
FIG. 6 shows a schematic flowchart for obtaining pathway measures corresponding to Ammonia releasing and Pyruvate pathways in accordance with an embodiment of the disclosure.

According to an embodiment of the disclosure, the system 100 is further configured to calculate the pathway ratios of the individual as shown in the schematic flowchart of FIG. 6. The pathway ratios are calculated using the first ratio calculation module 118 and the second ratio calculation module 120. As mentioned above in the present example, the set of Ammonia releasing pathways and Pyruvate pathway are being utilized to predict the gut health of the individual. As shown in FIG. 6, Lysine (L), Glutarate (G), Tetra-hydro folate (T) and Histidine (H) correspond to the set of Ammonia releasing pathways and Pyruvate (P) corresponds to Pyruvate pathway. The figure shows corresponding pathway abundances at two different time stamps T1 and T2, where V is corresponding value of the cumulative abundance of the taxa contributing to particular pathways. Initially, at step 402, for each of the Ammonia releasing pathways (L, G, T and H), a ratio $R_A$ (First ratio) of cumulative abundance of the taxa (having that pathway) at T1 and T2 is calculated using the Ammonia releasing pathway abundance calculation module 114. At step 404, it is checked that if $R_A$ is more than 1.5. If $R_A$ is more than 1.5 then at step 406 put the pathway abundance in group 1. If $R_A$ is less than 1.5 then at step 408 check if $R_A$ is less than 0.6. If $R_A$ is not less than 0.6, then at step 410 discard the $R_A$. If $R_A$ is less than 0.6, then at step 412 put the pathway abundance in group 2. At the next step 414, find group median abundance and select the group with higher value out of group 1 and 2. Finally at step 416, note the value of $R_A$ for the selected group and the group median abundance, referred to as 'Ammonia median' (AM).

Similarly, at step 418 the ratio $R_P$ (Second ratio) of cumulative abundance of the taxa corresponding to the Pyruvate pathway at T1 and T2 is calculated using the Pyruvate pathway abundance calculation module 116. At step 420, it is checked if the ratio $R_P$ is more than 1.5 or less than 0.6. If $R_P$ is neither more than 1.5 nor less than 0.6 then at step 422 discard $R_P$. If $R_P$ is either more than 1.5 or less than 0.6 then at step 424 note $R_P$ and group median abundance, referred to as 'Pyruvate median' (PM).

According to an embodiment of the disclosure, the system 100 also comprises the Ammonia median evaluation module 120 and the Pyruvate median evaluation module 122. The Ammonia median evaluation module 120 and the Pyruvate median evaluation module 122 are configured to calculate Ammonia median and the Pyruvate median respectively. The Ammonia median is the median value of abundance of bacterial taxa possessing the set of Ammonia releasing pathways. The Pyruvate median is the median value of abundance of bacterial taxa possessing Pyruvate to Butyrate pathway.

Figure 7:
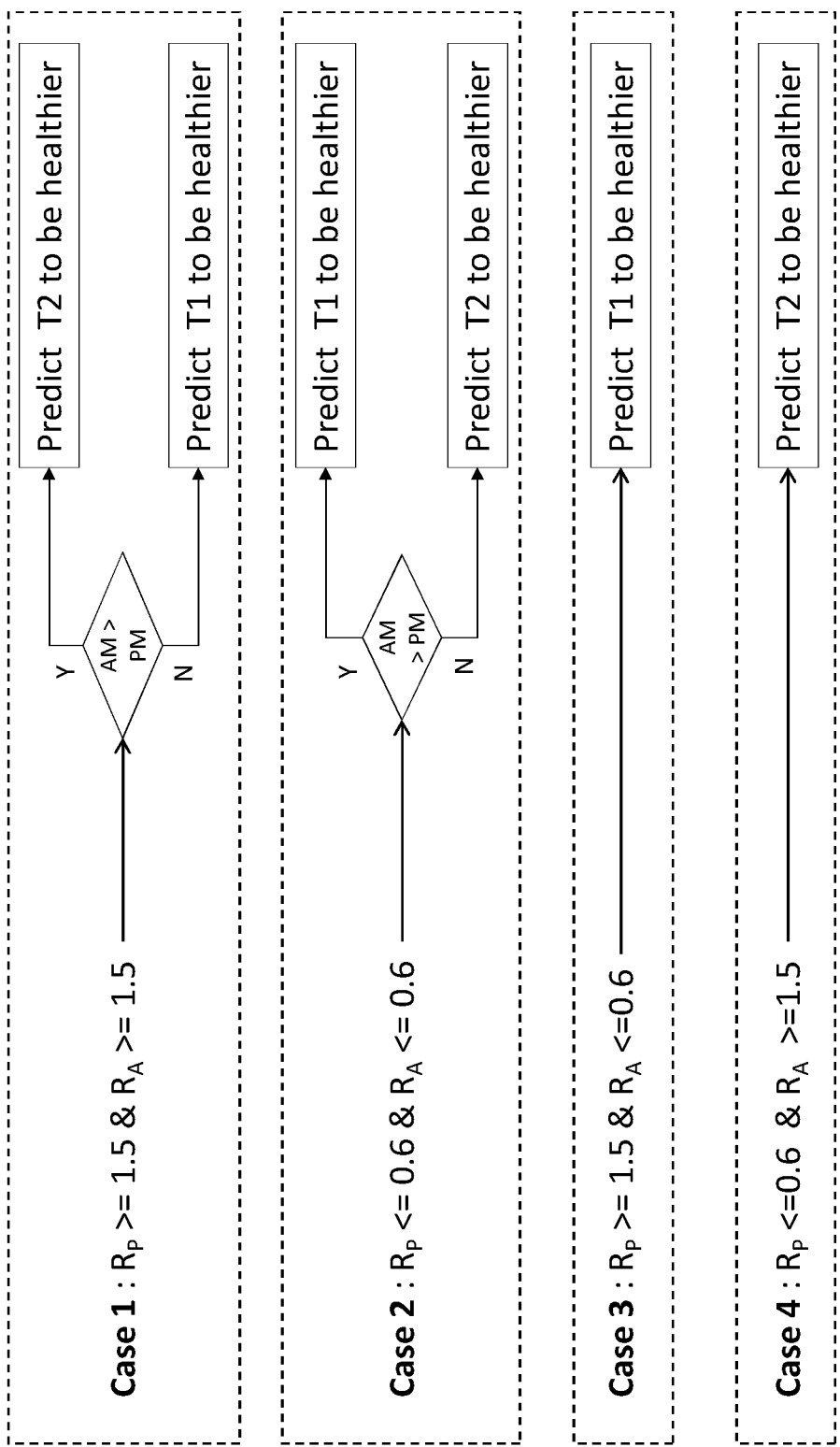
FIG. 7 shows a predefined criteria for predicting either T1 or T2 to be healthier as compared to each other in accordance with an embodiment of the present disclosure.

According to an embodiment of the disclosure the system 100 is further configured to predict the health of the individual based on the values of $R_A$, $R_P$, AM and PM based on a predefined set of criteria as also shown in FIG. 7. The predefined criteria is used by the health status prediction module 126 to determine the health of the person. The predefined criteria comprises predicting either T1 or T2 to be healthier as compared to each other based on the following condition:
predicting T2 as healthier, if both the ratios $R_A$ and $R_P$ are more than 1.5, and Ammonia median (AM) is greater than the Pyruvate median (PM);
predicting T1 is healthier, if both the ratios $R_A$ and $R_P$ are more than 1.5, and AM is less than the PM;
predicting T1 is healthier, if both the ratios $R_A$ and $R_P$ are less than 0.6 and AM is greater than the PM;
predicting T2 is healthier, if both the ratios $R_A$ and $R_P$ are less than 0.6 and Ammonia median is less than the Pyruvate median;
predicting T1 is healthier, if the first ratio $R_A$ is less than 0.6 and second ratio $R_P$ is more than 1.5; and
predicting T2 is healthier, if the first ratio $R_A$ is more than 1.5 and second ratio $R_P$ is less than 0.6.

It should be appreciated that the pathway abundance can also be predicted through various other techniques. In an embodiment, the taxonomic and gene abundance can be predicted using the metagenomic samples. This information can then be utilized for predicting pathway abundance and thereby monitoring gut health using the method and system discussed in the disclosure.

In another embodiment, the primers corresponding to each gene of the mentioned pathways can be amplified (through techniques like PCR). This information can then be utilized for predicting pathway abundance and thereby monitoring gut health using the method and system discussed in the invention. Thus the above two methods provide gene information, which would allow prediction of actual pathway abundance instead of inferring it from the taxonomic abundance.

In yet another embodiment, expression data of the constituent genes of the mentioned pathways can be utilized for predicting pathway abundance and thereby monitoring gut health using the method and system discussed in the disclosure.

Figure 8A:
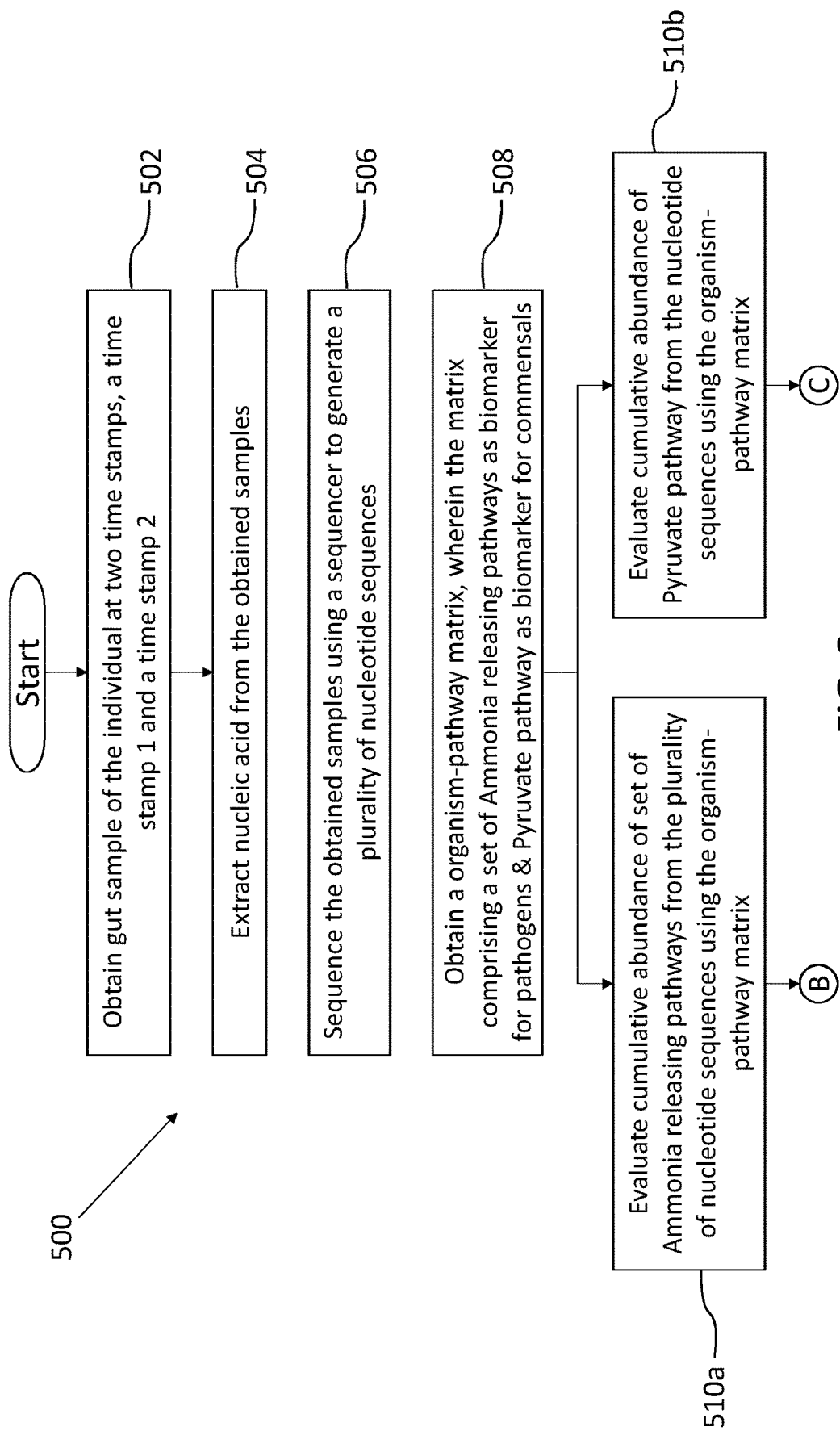
FIG. 8a-8b shows a flow chart illustrating the steps involved in predicting gut health of an individual in accordance with an embodiment of the disclosure.
Figure 8B:
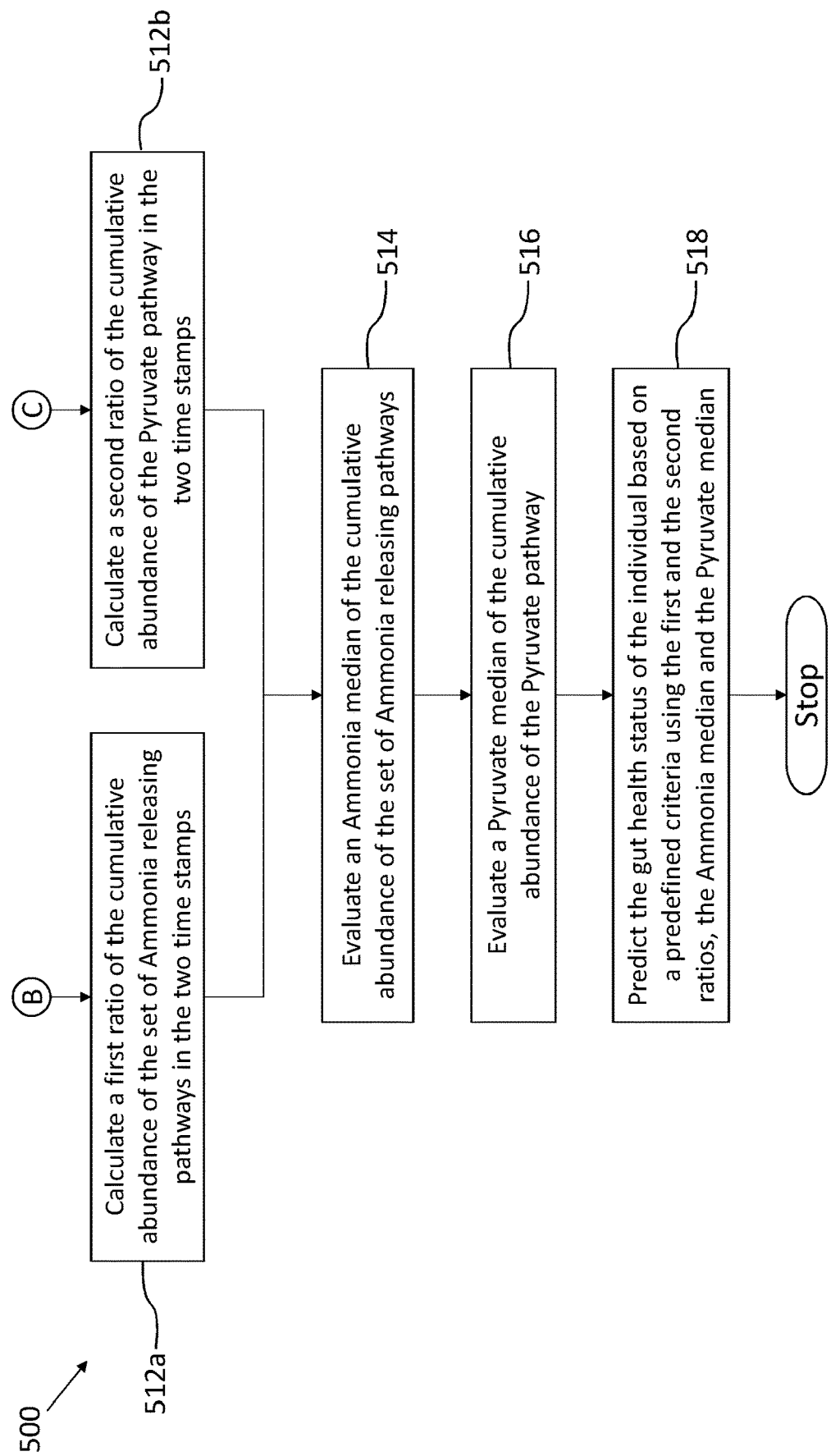

In operation, a flowchart 500 illustrating the steps involved for predicting gut health of the individual is shown in FIG. 8a-8b. Initially at step 502, gut sample of the individual is obtained at two time stamps, a time stamp 1 and a time stamp 2. In an example, samples may be obtained from two physiological conditions of the same person. At step 504, the nucleic acid is extracted from the obtained sample. And at step 506, the obtained sample are then sequenced using the sequencer 106 to generate the plurality of nucleotide sequences.

In the next step, 508 the organism-pathway matrix is obtained, wherein the matrix comprising a set of Ammonia releasing pathways as biomarker for pathogens and Pyruvate pathway as biomarker for commensals. The pathogen represents bacteria harmful to gut and commensal represents bacteria beneficial or symbiotic to gut.

At step 510a, the cumulative abundance of the set of Ammonia releasing pathways is obtained from the plurality of nucleotide sequences using the organism pathway matrix. Similarly at step 510b, the cumulative abundance of the Pyruvate pathway is obtained from the plurality of nucleotide sequences using the organism pathway matrix. Step 510a and 510b can be performed simultaneously. Though it should be appreciated that in another embodiment, any other pathways can also be utilized as biomarkers for pathogens or commensals. The cumulative abundance of bacterial taxa corresponding to a particular pathway is referred to as 'pathway abundance' throughout this embodiment. In the next step 512a, the first ratio of the cumulative abundance of the taxa at two time stamps is calculated for the set of Ammonia releasing pathways using the first ratio calculation module 118. And at step 512b, the second ratio of the cumulative abundance of the taxa at two time points is calculated corresponding to Pyruvate pathway using the second ratio calculation module 120.

In the next step 514, the Ammonia median of the cumulative abundance of the set of Ammonia releasing pathways is evaluated. Similarly, at step 516, the Pyruvate median of the cumulative abundance of the Pyruvate pathway is evaluated. And finally at step 518, the health status of the individual is predicted based on the predefined criteria using the first and the second ratios using the health status prediction module 118.

According to an embodiment of the disclosure, the system 100 can also be provided as a tool or kit for assessing the health of the individual. The tool may comprise an input module for receiving the gut samples as input. The tool further comprises the processor and the output module. The processor will process the input data and may display the health status of the individual on the output module.

According to an embodiment of the disclosure, the kit may contain two compartments where the first compartment may contain probes for marker gene (e.g. 16S rRNA) detection while the second compartment comprises a series of cDNA complementary to each gene (or part of the gene) constituting the pathways (pathway biomarkers) addressed in the present disclosure. This would allow prediction of pathway as well as taxonomy based changes between two time stamps. Further, the taxonomy based changes can be correlated to pathway changes in order to understand contribution of each taxa and devise more specific personalized therapeutic regime.

For the first compartment, the input can be extraction of marker genes for the gut samples of each of the time stamps followed by PCR amplification and sequencing. These amplicon when added to the compartment can be detected by signals like fluorophores, chemi-luminescence etc. While for the second compartment, the input can be mRNA/cDNA extraction from samples for each time point followed by hybridization to the corresponding cDNA probes complementary to pathway domains discussed above. The hybridization can be detected using visual signals like fluorophores, chemi-luminescence etc. and used as an indicator of the expression of each of the pathways and differential expression between two time stamps.

According to an embodiment of the disclosure, the system 100 can also be validated with the help of following experimental data:

Case Study 1

Figure 5A:
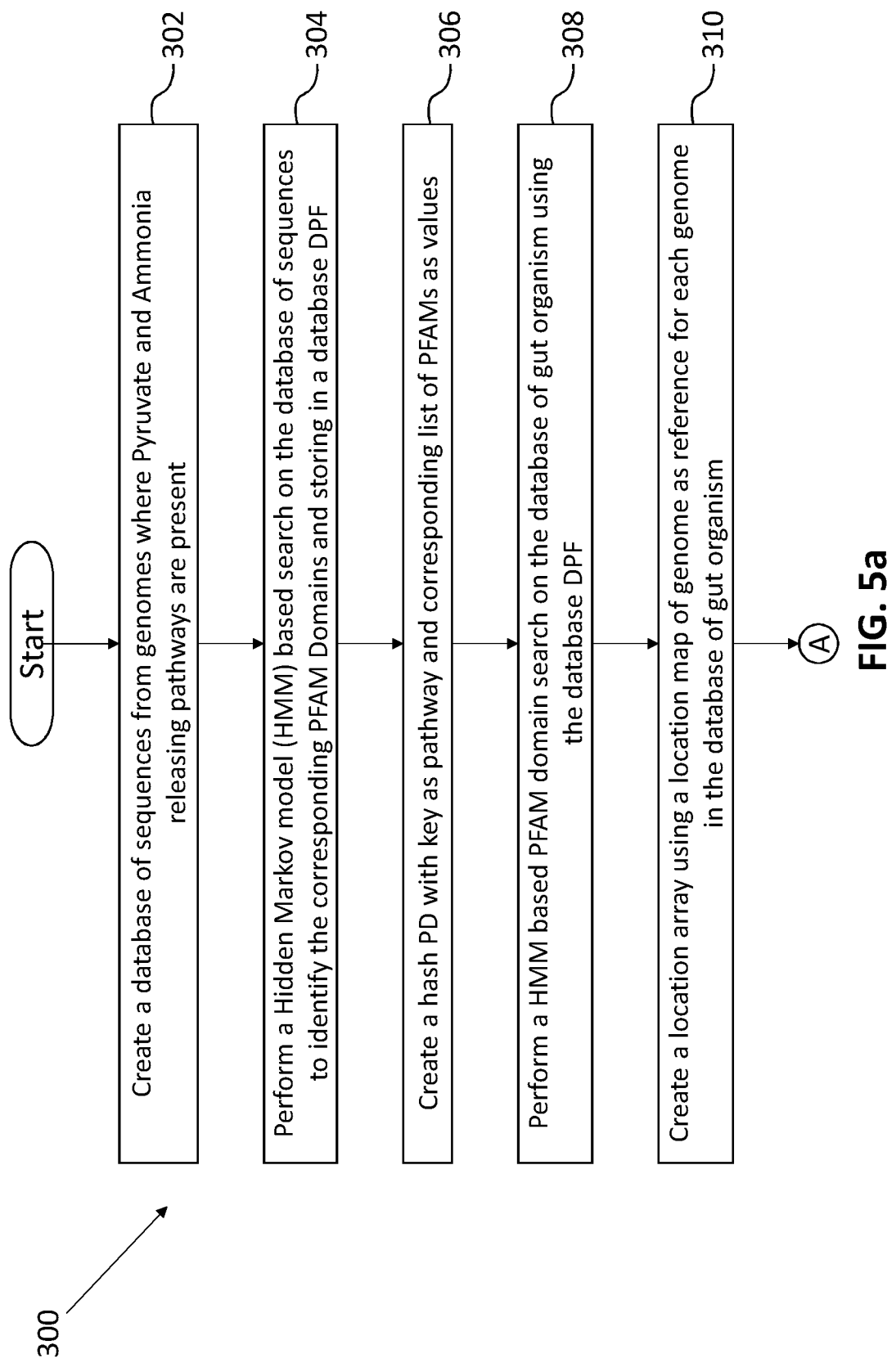
FIG. 5a-5b shows a flowchart for creating a 'organism-pathway' matrix according to an embodiment of the disclosure.
Figure 5B:
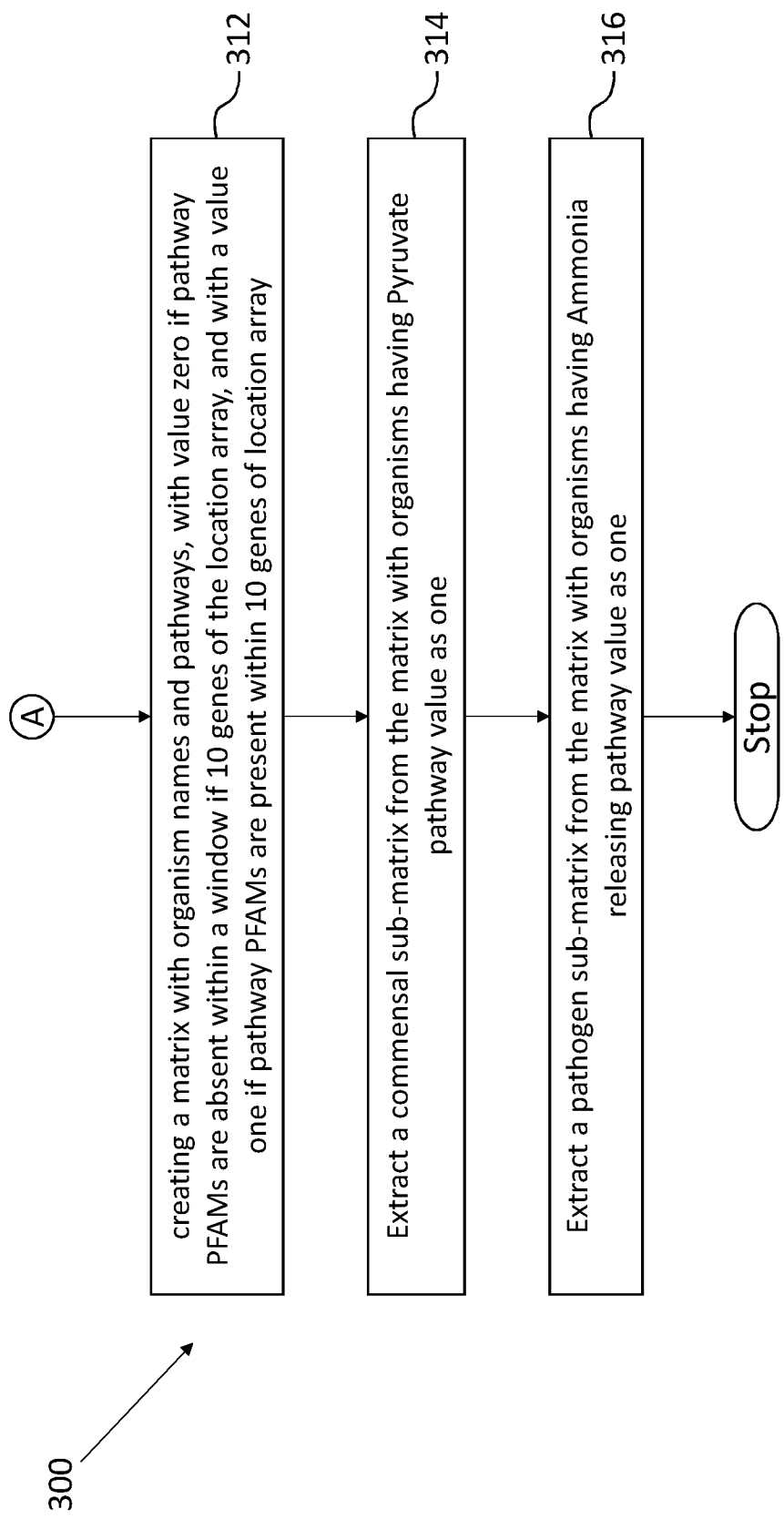

The dataset involves publicly available sequence data corresponding to representative gut microbiome samples obtained from 58 individuals suffering with colorectal cancer from Spanish population. Following research paper was referred to get the dataset: "Genomic analysis identifies association of *Fusobacterium* with colorectal carcinoma—by Kostic A D, Gevers D, Pedamallu C S, Michaud M, Duke F, Earl A M, Ojesina A I, Jung J, Bass A J, Tabernero J, Baselga J, Liu C, Shivdasani R A, Ogino S, Birren B W, Huttenhower C, Garrett W S, Meyerson M. 2012. Genome Res 22:292-298". For each subject, two sets of 16S rRNA sequences corresponding to the cancer affected region of the colon and the flanking unaffected region were considered. Taxonomic classification of the obtained sequences was performed using RDP classifier and taxonomic abundance matrix was obtained. This matrix was normalized and abundances of representative taxa for five pathways were extracted for further analysis. An example of the results obtained using methodology described in FIGS. 4 and 5 are discussed below using Sample C0355 from the studied dataset.

(i) Abundance Values Corresponding to Different Pathways in the Representative Sample

TABLE I

| | Pathway* | | | | |
| --- | --- | --- | --- | --- | --- |
| | L | G | T | H | P |
| Disease (T1) | $V_{L1}$ 0.257 | $V_{G1}$ 0.257 | $V_{T1}$ 0.004 | $V_{H1}$ 0.004 | $V_{P1}$ 0.065 |
| Healthy (T2) | $V_{L2}$ 0.03 | $V_{G2}$ 0.03 | $V_{T2}$ 0.001 | $V_{H2}$ 0.001 | $V_{P2}$ 0.176 |

The pathways represented by the abbreviations mentioned in the above table is as follows:

L: Lysine→Butyrate
G: Glutarate→Butyrate
T: Histidine→Tetra-hydro folate
H: Histidine→Glutamate
P: Pyruvate→Butyrate The table above indicates the total abundance of taxa containing each of the mentioned pathways. For example, the second column indicates that total normalized abundance of taxa possessing Lysine pathway in sample T1 is 0.257 ($V_{L1}$) while in sample T2 is 0.03 ($V_{L2}$). Similar values are depicted for other pathways ($V_{G1}$-$V_{G2}$, $V_{H1}$-$V_{H2}$, $V_{T1}$-$V_{T2}$, and $V_{P1}$-$V_{P2}$).

(ii) Ratio of Pathway Abundances in Input Sample at Two Time Stamps

The next step involves calculating fold change in abundance of each of these pathways between two samples.

|  | L | G | T | H | P |
|---|---|---|---|---|---|
| Ratio (R = T1/T2) | 8.705 | 8.705 | 3.776 | 3.776 | 0.369 |

Thus, the table above indicates that abundance of Lysine utilizing bacteria is ~8.7 times in T1 as compared to T2. Similar inferences can be made for other pathways. Note that, R of the Ammonia releasing pathways (Lysine, Glutarate, Histidine and THF), $R_A>1.5$ and, R of Pyruvate pathway $R_P<0.6$.

(iii) Prediction of Gut Health Status (GHS)

As can be noticed, although there is around four times change in abundance of Histidine pathway, the average abundance of these pathways in both metagenomic samples is very less (0.004 in T1 and 0.001 in T2). On the contrary, the abundance of Lysine pathway is very high in addition to its ratio being high (~8.7). These observations indicate that weightage should be given to the normalized abundance of a pathway (considering both samples) in addition to the ratio. Thus, average abundance of each of the pathway in both samples (T1 and T2) was accounted for while predicting gut health status. For Ammonia releasing pathways (Lysine, Glutarate, Histidine and THF) groups were formed based on the values of $R_A$ (ratio). Since values for all the four pathways are greater than 1.5, all four of them were included in Group 1. Further, the $R_P$ was obtained as <0.6. Thus, since $R_P<0.6$ and $R_A>1.5$ (case 4 in FIG. 6), the sample corresponding to T2 is predicted to be healthier than T1.

This prediction is in line with the metadata provided with this study for sample C0355 where Sample 1 and Sample 2 correspond to CRC and normal samples respectively. Similar analysis was performed on all 58 samples in the study. Results show that in most samples (70.69%), both commensal as well as pathogenic pathway biomarkers are capable of capturing the gut health status. In the rest of the cases (29.31%), the gut health status could be predicted based on any one of the two pathway biomarkers.

Case Study 2

Datasets used in this study comprised of fecal samples from 14 individuals belonging to US state of Minnesota suffering with *Clostridium difficile* infection (CDI). Following research paper was referred to get the dataset: "Recovery of the Gut Microbiome following Fecal Microbiota Transplantation—by Seekatz, A. M., Aas, J., Gessert, C. E., Rubin, T. A., Saman, D. M., Bakken, J. S., and Young, V. B. 2014. mBio 5: e00893-14. These patients were subjected to an antibiotic treatment followed by fecal microbiome transplantation. We evaluated the changes in gut health for these samples using our novel GHS prediction scheme. Results show that both commensal as well as pathogenic pathway biomarkers are capable of capturing the gut health status in 64.3% of the samples while for the rest of the cases (35.7%), at least one of the pathway biomarkers could predict the gut health status.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

The embodiments of present disclosure herein provide system and method for predicting the gut health of the individual.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A method for predicting gut health of an individual using non-invasive techniques, the method comprising the steps of:

receiving gut samples of the individual at two time stamps, a time stamp 1 and a time stamp 2 or receiving at least two gut samples from at least two individuals as a sample 1 and a sample 2;

extracting nucleic acid from the obtained samples;

generating a plurality of nucleotide sequences from the extracted nucleic acid samples;

generating a taxonomic abundance matrix for each of the gut samples, by calculating abundances of a plurality of bacterial taxa within each of the gut samples using the extracted nucleotide sequences;

creating an 'organism-pathway matrix' by:

listing protein sequences pertaining to proteins which catalyze reactions from Pyruvate to Butyrate pathway as a biomarker for commensal gut bacteria and proteins which catalyze reactions from a set of Ammonia releasing pathways as a biomarker for pathogenic gut bacteria;

identifying protein domains pertaining to the listed protein sequences;

accessing a database of genomes;

selecting genomes from the database belonging to human gut microbiota;

creating a location array 'LAG' for the selected genomes;

creating a hash PD with a key 'P' as a pathway and corresponding obtained list of protein domains as values for each pathway;

creating the 'organism-pathway matrix' by performing a protein domain search for the each pathway P from the hash PD on the protein sequences of the genome G using the identified protein domains to check presence of the respective protein domains values pertaining to the pathway P on the Genome G using the location array 'LAG' of the Genome G as a reference, wherein the presence of the respective protein domains values on the Genome G indicates presence of the pathway, wherein a value of 'one' is mentioned in the organism pathway matrix which is indicative of presence of the pathway and a value of 'zero' is mentioned in the organism pathway matrix which is indicative of absence of the pathway, wherein for each pathway P a value of 'one' is assigned if for each pathway P in the hash PD when all the protein domains values mentioned in the hash PD lie within protein domains corresponding to the protein sequences encoded in consecutively occurring 10 genes on the genome G, and for each pathway P, a value of 'zero' is assigned if for each pathway P in the hash PD, all the protein domains values do not lie within the protein domains corresponding to the protein sequences encoded in the consecutively occurring 10 genes on the genome G, wherein the set of Ammonia releasing pathways correspond to the proteins catalyzing reactions consisted in the set of Ammonia releasing pathways, wherein the set of Ammonia releasing pathways consist of proteins catalyzing reactions pertaining to Histidine to Glutamate, Histidine to Tetrahydro-folate (THF), Lysine to Butyrate and Glutarate to Butyrate pathways, and wherein the Pyruvate to Butyrate pathway corresponds to the proteins catalyzing reaction consisted in the Pyruvate to Butyrate pathway, wherein the Pyruvate to Butyrate pathway consists of conversion of Pyruvate to Acetyl-CoA, Acetyl-CoA to Acetoacetyl-CoA, Acetoacetyl-CoA to 3-hydroxybutanoyl-CoA, 3-hydroxybutanoyl-CoA to Crotonyl-CoA, Crotonyl-CoA to Butyryl-CoA and Butyryl-CoA to Butyrate, wherein the Histidine to Glutamate pathway consists of conversion of L-Histidine to Urocanate, Urocanate to 4-Imidazolone-5-propanoate, 4-Imidazolone-5-propanoate to N-Formimino-L-glutamate, N-Formimino-L-glutamate to L-Glutamate, wherein Histidine to Tetrahydrofolate pathway consists of conversion of L-Histidine to Urocanate, Urocanate to 4-Imidazolone-5-propanoate, 4-Imidazolone-5-propanoate to N-Formimino-L-glutamate, N-Formimino-L-glutamate to N-Formimino-tetrahydrofolate and N-Formimino-tetrahydrofolate to 5,10-Methyl-tetrahydrofolate, wherein Lysine to Butyrate pathway consists of conversion of Lysine to β-Lysine, β-Lysine to 3,5-Diaminohexanoate, 3,5-Diaminohexanoate to 3-Keto-5-aminohexanoate, 3-Keto-5-aminohexanoate to 3-Aminobutyryl-CoA, 3-Aminobutyryl-CoA to Crotonyl-CoA, Crotonyl-CoA to Butyryl-CoA and Butyryl-CoA to Butyrate, wherein Glutarate to Butyrate pathway consists of conversion of Glutarate to 2-Oxoglutarate, 2-Oxoglutarate to 2-Hydroxyglutarate, 2-Hydroxyglutarate to 2-Hydroxyglutaryl-CoA, 2-Hydroxyglutaryl-CoA to Glutaconyl-CoA, Glutaconyl-CoA to Crotonyl-CoA, Crotonyl-CoA to Butyryl-CoA and Butyryl-CoA to Butyrate;

calculating cumulative abundance of bacterial taxa present in each of the gut samples for each Ammonia releasing pathway of the set of Ammonia releasing pathways using the taxonomic abundance matrix and the 'organism-pathway matrix' comprises:

obtaining a pathogen sub-matrix from the organism-pathway matrix by extracting a sub-matrix corresponding to the gut organisms having Ammonia releasing pathway values as one;

calculating cumulative abundance of the bacterial taxa present in each of the gut samples for the Pyruvate to Butyrate pathway using the taxonomic abundance matrix and the 'organism-pathway matrix' comprises:

obtaining a commensal sub-matrix from the organism-pathway matrix by extracting a sub-matrix corresponding to the gut organisms having Pyruvate to Butyrate pathway value as one; and calculating the cumulative abundance of the bacterial taxa as follows when the sample has been sequenced using at least one of amplicon sequencing, whole genome sequencing or metagenomic sequencing:

obtaining a first input matrix of bacterial genus abundance for the gut sample at the time stamp 1 or from the sample 1;

obtaining a second input matrix of bacterial genus abundance for the gut sample at time stamp 2 or from the sample 2;

calculating the cumulative abundance of the bacterial taxa for the commensal pathway for the first input matrix by multiplying the commensal sub-matrix and the first input matrix;

calculating the cumulative abundance of the bacterial taxa for the commensal pathway for the second input matrix by multiplying the commensal sub-matrix and the second input matrix;

calculating the cumulative abundance of the bacterial taxa for the pathogen pathways for the first input matrix by multiplying the pathogen sub-matrix and the first input matrix; and calculating the cumulative abundance of the bacterial taxa for the pathogen pathways for the second input matrix by multiplying the pathogen sub-matrix and the second input matrix;

calculating a ratio of the cumulative abundance of the bacterial taxa separately for each of the set of Ammonia releasing pathways based on the values in the two time stamps or the values in the two samples, the sample 1 and the sample 2 and selecting first ratio ($R_A$) by, checking for each of the Ammonia releasing pathway if the ratio is more than 1.5, if yes then putting the Ammonia releasing pathway in group 1, else checking if the ratio is less than 0.6, if yes, then putting the Ammonia releasing pathway in group 2;

calculating a 'group median abundance' as a median of the cumulative abundance values of the Ammonia releasing pathways in the group 1, and calculating a 'group median abundance' as a median of the cumulative abundance values of the Ammonia releasing pathways in the group 2;

selecting the group with higher median value out of the groups 1 and 2; and selecting the ratios of the Ammonia releasing pathways from the selected group as the first ratio ($R_A$);

calculating a second ratio ($R_P$) of the cumulative abundance of the bacterial taxa for the Pyruvate to Butyrate pathway based on the values in the two time stamps or the values in the two samples, and selecting the second ratio ($R_P$) by checking if the ratio is more than 1.5 or less than 0.6, and if ($R_P$) is neither more than 1.5 nor less than 0.6, then discarding ($R_P$); else if ($R_P$) is either more than 1.5 or less than 0.6 then ($R_P$), then selecting the second ratio ($R_P$);

calculating an Ammonia median of the cumulative abundance of the bacterial taxa of each of the set of Ammonia releasing pathways corresponding to the two time stamps or the two samples, wherein the Ammonia median is a median value of the cumulative abundance of the bacterial taxa of the set of Ammonia releasing pathways OR selecting the 'Ammonia median' as the group median abundance value of the selected group from the group 1 and 2; and selecting a value of the cumulative abundance of the bacterial taxa of the Pyruvate to Butyrate pathway as the Pyruvate median;

predicting the gut health status of the individual based on a predefined criteria using the first and the second ratios, the Ammonia median and the Pyruvate median, wherein the predefined criteria comprises:

predicting time stamp 2 or the sample 2 is healthier, if the first ratio is more than 1.5 and second ratio is more than 1.5 and the Ammonia median is more than the Pyruvate median;

predicting time stamp 1 or the sample 1 is healthier, if the first ratio is more than 1.5 and second ratio is more than 1.5 and the Ammonia median is less than the Pyruvate median;

predicting time stamp 1 or the sample 1 is healthier, if the first ratio is less than 0.6 and second ratio is less than 0.6 and the Ammonia median is more than the Pyruvate median;

predicting time stamp 2 or the sample 2 is healthier, if the first ratio is less than 0.6 and second ratio is less than 0.6 and the Ammonia median is less than the Pyruvate median;

predicting time stamp 1 or the sample 1 is healthier, if the first ratio is less than 0.6 and second ratio is more than 1.5; and predicting time stamp 2 or the sample 2 is healthier, if the first ratio is more than 1.5 and second ratio is less than 0.6; and categorizing the individual or the at least two individuals in a healthy state or dysbiotic diseased state based on the predicted gut health status of the individual or the at least two individuals respectively, and providing at least one of personalized therapeutics, antibiotic treatment or fecal microbiome transplantation to the individual based on the predicted gut health status.

2. The method of claim 1, wherein the gut samples are obtained from at least one of stool, intestinal swab, intestinal tissue or intestinal fluid of the individual.

3. The method of claim 1, wherein the time stamp 1 and the time stamp 2 indicate two different time points.

4. The method of claim 1 wherein the Sample 1 and Sample 2 are corresponding to the at least two individuals pertaining to two different population where, the gut health status of two population are being compared.

5. The method of claim 1, wherein the nucleic acid comprises any one of a Deoxyribonucleic acid (DNA) or a Ribonucleic acid (RNA).

6. The method of claim 1, wherein the plurality of nucleotide sequences are generated through at least one of:
an amplicon sequencing based on 16S rRNA gene or any other bacterial taxonomic marker gene,
a whole genome sequencing or metagenomic sequencing,
a PCR (Polymerase Chain Reaction) technique employed for targeted sequencing of genes of the pathways, or
a Microarray or RNA-sequencing techniques employed for measuring gene expression level.

7. A system for predicting gut health of an individual using non-invasive techniques, the system comprises:
an input module for obtaining gut samples of the individual at two time stamps, a time stamp 1 and a time stamp 2 or receiving at least two gut samples from at least two individuals as a sample 1 and a sample 2;
an extractor for extracting nucleic acid from the obtained samples;
a sequencer for sequencing the sample to generate a plurality of nucleotide sequences;
a memory; and
a processor in communication with the memory, wherein the processor further configured to:
create an 'organism-pathway matrix' by:
listing protein sequences pertaining to protein catalyzing reactions from Pyruvate to Butyrate pathway as a biomarker for commensal gut bacteria and protein catalyzing reactions from a set of Ammonia releasing pathways as a biomarker for pathogenic gut bacteria;
identify protein Domains pertaining to the listed protein sequences;
accessing a database of genomes;
selecting genomes from the database belonging to human gut microbiota;
creating a location array 'LAG' for the selected genomes;
creating a hash PD with a key 'P' as a pathway and corresponding obtained list of protein domains as values for each pathway; and
creating the 'organism-pathway matrix' by performing a protein domain search for each pathway P from the hash PD on the protein sequences of the genome G using the identified protein domains—to check presence of the respective protein domains values of the pathway P on the Genome G using the location array 'LAG' of the Genome G as a reference, wherein the presence of the respective protein domains values on the Genome G indicates presence of the pathway, wherein a value of 'one' is mentioned in the organism pathway matrix which is indicative of presence of the pathway and a value of 'zero' is mentioned in the organism pathway matrix which is indicative of absence of the pathway, wherein for each pathway P in the hash PD when all the protein domains values mentioned in the hash PD lie within protein domains corresponding to the protein sequences encoded in consecutively occurring 10 genes on the genome G and for each pathway reaction P a value of 'zero' is assigned if for each pathway P in the hash PD, all the protein domains values do not lie within protein domains corresponding to the protein sequences encoded in consecutively occurring 10 genes on the genome G, wherein the set of Ammonia releasing pathways correspond to the proteins catalyzing reactions consisted in the set of Ammonia releasing pathways, wherein the set of Ammonia releasing pathways consist of Histidine to Glutamate, Histidine to Tetrahydro-folate (THF), Lysine to Butyrate and Glutarate to Butyrate pathways, and wherein the Pyruvate to Butyrate pathway corresponds to proteins catalyzing reactions consisted in the Pyruvate to Butyrate pathway, wherein the Pyruvate to Butyrate pathway consist of conversion of Pyruvate to Acetyl-CoA, Acetyl-CoA to Acetoacetyl-CoA, Acetoacetyl-CoA to 3-hydroxybutanoyl-CoA, 3-hydroxybutanoyl-CoA to Crotonyl-CoA, Crotonyl-CoA to Butyryl-CoA and Butyryl-CoA to Butyrate, wherein the Histidine to Glutamate pathway consist of conversion of L-Histidine to Urocanate, Urocanate to 4-Imidazolone-5-propanoate, 4-Imidazolone-5-propanoate to N-Formimino-L-glutamate, N-Formimino-L-glutamate to L-Glutamate, wherein Histidine to Tetrahydrofolate pathway consist of conversion of L-Histidine to Urocanate, Urocanate to 4-Imidazolone-5-propanoate, 4-Imidazolone-5-propanoate to N-Formimino-L-glutamate, N-Formimino-L-glutamate to N-Formimino-tetrahydrofolate and N-Formimino-tetrahydrofolate to 5,10-Methyl-tetrahydrofolate, wherein Lysine to Butyrate pathway consist of conversion of Lysine to β-Lysine, β-Lysine to 3,5-Diaminohexanoate, 3,5-Diaminohexanoate to 3-Keto-5-aminohexanoate, 3-Keto-5-aminohexanoate to 3-Aminobutyryl-CoA, 3-Aminobutyryl-CoA to Crotonyl-CoA, Crotonyl-CoA to Butyryl-CoA and Butyryl-CoA to Butyrate, wherein Glutarate to Butyrate pathway consist of conversion of Glutarate to 2-Oxoglutarate, 2-Oxoglutarate to 2-Hydroxyglutarate, 2-Hydroxyglutarate to 2-Hydroxyglutaryl-CoA, 2-Hydroxyglutaryl-CoA to Glutaconyl-CoA, Glutaconyl-CoA to Crotonyl-CoA, Crotonyl-CoA to Butyryl-CoA and Butyryl-CoA to Butyrate;

calculate cumulative abundance of bacterial taxa present in each of the gut samples for each Ammonia releasing pathway of the set of Ammonia releasing pathways using a taxonomic abundance matrix and the 'organism-pathway matrix' comprises:

obtaining a pathogen sub-matrix from the organism-pathway matrix by extracting a sub-matrix corresponding to the gut organisms having Ammonia releasing pathway values as one, wherein the taxonomic abundance matrix for each of the gut samples, is generated by calculating abundances of a plurality of bacterial taxa within each of the gut samples using the generated nucleotide sequences;

calculate cumulative abundance of the bacterial taxa present in each of the gut samples for the Pyruvate to Butyrate pathway using the taxonomic abundance matrix and the 'organism-pathway matrix' comprises:

obtaining a commensal sub-matrix from the organism-pathway matrix by extracting a sub-matrix corresponding to the gut organisms having Pyruvate to Butyrate pathway value as one;

calculating the cumulative abundance of the bacterial taxa as follows when the gut sample has been sequenced using at least one of amplicon sequencing, whole genome sequencing or metagenomic sequencing:

obtaining a first input matrix of bacterial genus abundance for an individual at the time stamp 1 or from the sample 1;

obtaining a second input matrix of bacterial genus abundance for the individual at time stamp 2 or from the sample 2;

calculating the cumulative abundance of the bacterial taxa for the commensal pathway for the first input matrix by multiplying the commensal sub-matrix and the first input matrix;

calculating the cumulative abundance of the bacterial taxa for the commensal pathway for the second input matrix by multiplying the commensal sub-matrix and the second input matrix;

calculating the cumulative abundance of the bacterial taxa for the pathogen pathways for the first input matrix by multiplying the pathogen sub-matrix and the first input matrix; and calculating the cumulative abundance of the bacterial taxa for the pathogen pathways for the second input matrix by multiplying the pathogen sub-matrix and the second input matrix;

calculate a ratio of the cumulative abundance of the bacterial taxa separately for each of set of Ammonia releasing pathways based on the values in the two time stamps or the values in the two samples, the sample 1 and the sample 2 and select first ratio ($R_A$) by, checking for each of the Ammonia releasing pathway if the ratio is more than 1.5, if yes then put the Ammonia releasing pathway in group 1, else check if the ratio is less than 0.6, if yes, then put the Ammonia releasing pathway in group 2;

calculating a 'group median abundance' as a median of the cumulative abundance values of the Ammonia releasing pathways in the group 1, and calculating a 'group median abundance' as a median of the cumulative abundance values of the Ammonia releasing pathways in the group 2;

selecting the group with higher median value out of the groups 1 and 2; and selecting the ratios of the Ammonia releasing pathways from the selected group as the first ratio ($R_A$);

calculate a second ratio ($R_P$) of the cumulative abundance of the bacterial taxa for the Pyruvate to Butyrate pathway based on the values in the two time stamps or the values in the two samples, and select the second ratio ($R_P$) by checking if the ratio is more than 1.5 or less than 0.6, and if ($R_P$) is neither more than 1.5 nor less than 0.6 then discarding ($R_P$); else if ($R_P$) is either more than 1.5 or less than 0.6 then ($R_P$) then selecting the second ratio ($R_P$);

calculate an Ammonia median of the cumulative abundance of the bacterial taxa of each of the set of Ammonia releasing pathways corresponding to the two time stamps or the two samples, wherein the Ammonia median is a median value of the cumulative abundance of the bacterial taxa of the set of Ammonia releasing pathways OR selecting the 'Ammonia median' as the group median abundance value of the selected group from the group 1 and 2; and selecting a value of the cumulative abundance of the bacterial taxa of the Pyruvate to Butyrate pathway as the Pyruvate median;

predict the gut health status of the individual based on a predefined criteria using the first and the second ratios, the Ammonia median and the Pyruvate median, wherein the predefined criteria comprises:
- predicting time stamp 2 or the sample 2 is healthier, if the first ratio is more than 1.5 and second ratio is more than 1.5 and the Ammonia median is more than the Pyruvate median;
- predicting time stamp 1 or the sample 1 is healthier, if the first ratio is more than 1.5 and second ratio is more than 1.5 and the Ammonia median is less than the Pyruvate median;
- predicting time stamp 1 or the sample 1 is healthier, if the first ratio is less than 0.6 and second ratio is less than 0.6 and the Ammonia median is more than the Pyruvate median;
- predicting time stamp 2 or the sample 2 is healthier, if the first ratio is less than 0.6 and second ratio is less than 0.6 and the Ammonia median is less than the Pyruvate median;
- predicting time stamp 1 or the sample 1 is healthier, if the first ratio is less than 0.6 and second ratio is more than 1.5; and
- predicting time stamp 2 or the sample 2 is healthier, if the first ratio is more than 1.5 and second ratio is less than 0.6; and an output module to categorize the individual or the at least two individuals in a healthy state or dysbiotic diseased state based on the predicted gut health status of the individual or of the at least two individuals respectively and providing at least one of personalized therapeutics, antibiotic treatment or fecal microbiome transplantation to the individual based on the predicted gut health status.

8. A kit for predicting gut health of an individual, comprising:
- an input module for receiving an input sample;
- a processor configured to analyze the input sample using the method performed in any of the claims 1, 2-3, 5-7, wherein the processor further comprising:
  - a first compartment for detecting the marker gene, and
  - a second compartment comprising a series of cDNA complementary to each domain constituting a plurality of pathways; and
- an output module for
  - displaying the health of the individual based on the analysis of the processor;
  - categorizing the individual or the at least two individuals in a healthy state or dysbiotic diseased state based on the predicted gut health status of the individual or of the at least two individuals respectively; and
  - providing at least one of personalized therapeutics, antibiotic treatment or fecal microbiome transplantation to the individual based on the predicted gut health status.

\* \* \* \* \*